United States Patent [19]

Hunt

[11] 4,269,183

[45] May 26, 1981

[54] COLD WEATHER BREATHING MASK

[76] Inventor: Patrick T. Hunt, R.R. 1, Smithville, Mo. 64089

[21] Appl. No.: 121,119

[22] Filed: Feb. 13, 1980

Related U.S. Application Data

[63] Continuation-in-part of Ser. No. 24,168, Mar. 26, 1979, abandoned.

[51] Int. Cl.³ ............................................ A61M 15/00
[52] U.S. Cl. ............................ 128/201.13; 128/204.17
[58] Field of Search ...................... 128/201.13, 204.17, 128/205.13, 205.17, 202.26

[56] References Cited

U.S. PATENT DOCUMENTS

| | | | |
|---|---|---|---|
| 2,741,246 | 4/1956 | Litchfield | 128/201.13 |
| 4,197,841 | 4/1980 | Brauer et al. | 128/201.13 |

*Primary Examiner*—Henry J. Recla
*Attorney, Agent, or Firm*—Lowe, Kokjer, Kircher, Wharton & Bowman

[57] ABSTRACT

A method and device for use in breathing where the ambient temperature is uncomfortable is the subject of the present invention. An air intake conduit is enclosed by a sack and communicates with a face mask that covers the nose and mouth of the wearer. Both the intake conduit and the enclosing sack extend in a curvilinear path over the head of the wearer to take advantage of heat normally lost through the head. A head covering may be used to further increase the efficiency of the heat exchange between the head and the air passing through the sack and the intake conduit. One-way valves on the inlet and outlet openings assure segregation of inhaled and exhaled air. Exhaled air is passed into the sack where it is held in heat exchange relationship with the incoming air moving through the conduit as well as with body heat radiated by the wearer's head. An exit opening at the end of the sack distal from the point where exhaled air enters allows the exhaled air to eventually pass from the sack.

10 Claims, 4 Drawing Figures

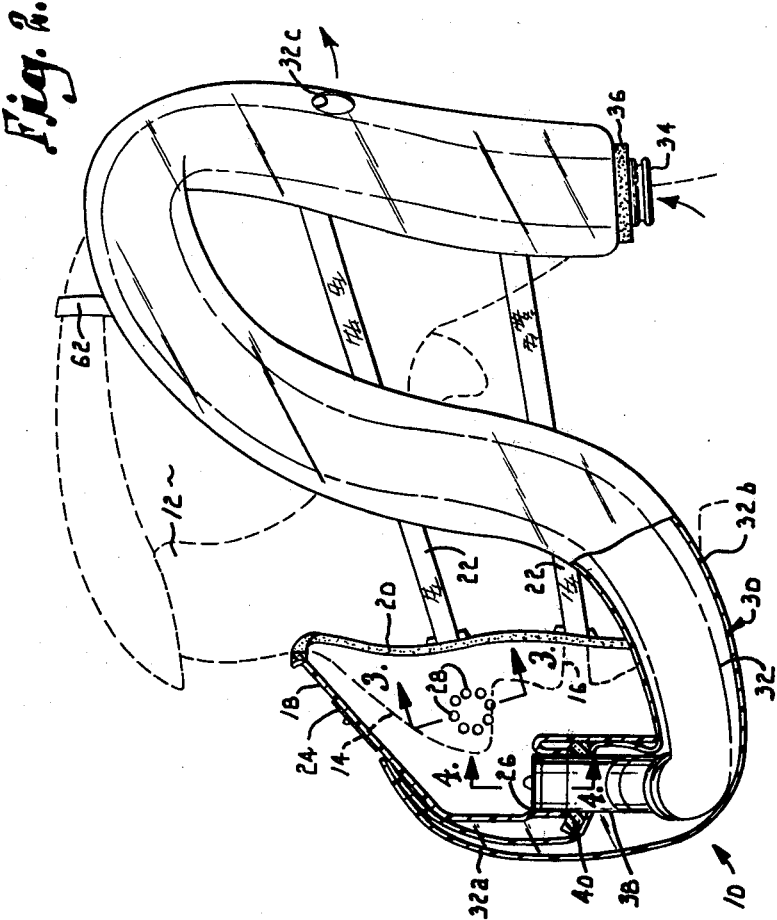
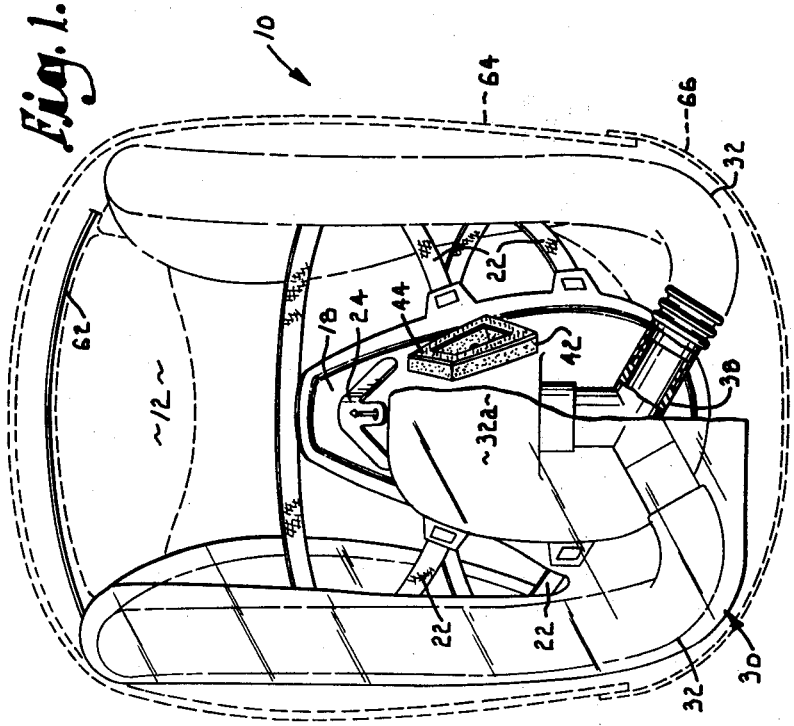
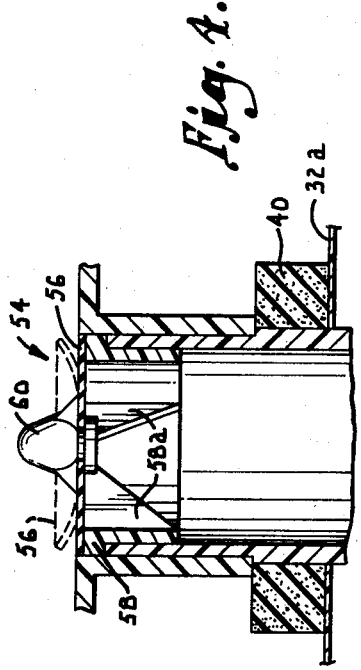
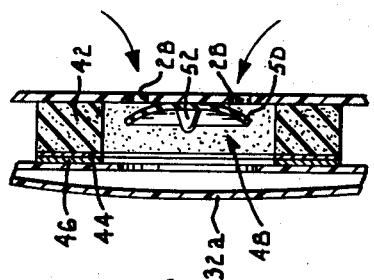

COLD WEATHER BREATHING MASK

This is a continuation-in-part application of Ser. No. 24,168, filed March 26, 1979 now abandoned.

SUMMARY AND BRIEF DESCRIPTION OF THE INVENTION

This invention relates to breathing devices generally and, more particularly, to a method and device which utilizes both the heat from exhaled air as well as body heat normally lost through radiation from the head for adjusting the temperature of air to be inhaled.

Cold weather breathing masks for use by individuals have previously been known. Examples of the prior art devices are found in U.S. Pat. Nos. 3,491,754; 3,707,966 and 4,062,359. All of the devices shown and described in the referenced patents utilize some type of tube or conduit which is positioned next to the body for heat exchange relationship therewith. Thus, the body heat warms incoming air prior to being inhaled by the wearer.

Another device of the prior art utilizes exhaled air to provide heat for a chemical reaction. This device is shown and described in U.S. Pat. No. 3,229,681.

Yet another device of the prior art is illustrated in German Patent No. 2,720,681. In the German reference, exhaled air is utilized to warm a mechanical filter through which inhaled air passes.

Still another device of the prior art as disclosed in U.S. Pat. No. 4,150,671 uses solely exhaled air to condition incoming air (but employs a length and caliber of incoming tubing rendering it ineffective as the diameter is significantly smaller than that of the adult human trachea). More importantly, it does not employ any contribution of body heat.

None of the devices of the prior art employ a simple heat exchange bag which is used in conjunction with an intake conduit to warm incoming air. Even more importantly, none of the devices of the prior art take advantage of the substantial heat loss which occurs through the head in order to warm incoming air. It is a known fact that approximately fifty percent (50%) of all body heat is lost through the head.

It is, therefore, a primary object of the present invention to provide a method and device which utilizes both warm exhaled air in conjunction with body heat lost through the head to warm incoming air before it is inhaled thereby making a more efficient and adequate warming of ambient air than possible with prior art devices.

Still another objective of my invention is to provide a method and device as described in the foregoing object which incorporates a mask where water vapor is collected for partial humidification of incoming air.

A particularly advantageous feature of the present invention is that it may be utilized without any filter element or a filter may be incorporated into the intake air conduit when necessary or desired.

Other objects of the invention will be made clear or become apparent from the following description and claims when read in light of the accompanying drawing, wherein:

FIG. 1 is a front elevational view of the device of the invention as it would appear in place on the head of a user;

FIG. 2 is a side elevational view of the device of FIG. 1 with portions being broken away and shown in cross section for purposes of illustration;

FIG. 3 is a generally vertical cross-sectional view on an enlarged scale taken along line 3—3 of FIG. 2; and FIG. 4 is another enlarged vertical cross-sectional view taken along 4—4 of FIG. 2.

Referring initially to FIGS. 1 and 2, the device of the present invention is designated generally by the numeral 10 and is intended to be worn around the head 12 of a person. The nose and mouth of the wearer are shown in broken lines in FIG. 2 and designated by the numerals 14 and 16, respectively.

Device 10 comprises a mask member 18 which is contoured to fit over the nose and mouth. The peripheral edge of mask 18 is provided with a strip of resilient foam 20 for assuring a relatively air-tight fit. Straps 22 hold the mask in tight engagement with the head 12. A metal t-bar 24 may be bent to conform to the configuration of the nose of a particular wearer to help assure proper fit. Mask 18 has an inlet opening 26 and two groupings of outlet openings each of which is designated by the numeral 28. Manifestly, one set of openings 28 is located on each side of nose 14.

Releasably coupled with mask 18 is an elongated plastic sack 30 which encases first and second flexible conduits 32. Sack 30 includes a central manifold portion 32a and conduit covering portions 32b. Two outlet openings 32c are located at the ends of portions 32b distal from the corresponding portion 32b of the sack to present an intake opening 34. This end of the conduit is sealingly joined to the sack by an adhesively secured rubber gasket 36.

A Y-coupling 38 is disposed in communication with inlet opening 26 and is coupled with each of the conduits 32 in the manner best illustrated in FIG. 1. An adhesively secured rubber gasket 40 holds coupling 38 in place.

Another rubber gasket 42 is secured to mask 18 adjacent each set of outlet openings 28 and is provided with a releasable fastener 44 such as the interlocking cloth type material sold under the trademark Velcro. A similar complemental fastening strip 46 is adhesively secured to the inside of manifold portion 32a of sack 30 (see FIG. 3). While the means for coupling manifold portion 32a to outlet openings 28 is shown for only one side of the mask, it is to be understood that a similar coupling is employed for the outlet openings on the opposite side.

Referring now in greater detail to FIG. 3, each series of outlet openings 28 is provided with a one-way valve designated generally by the numeral 48. Valve 48 comprises simply a flexible light weight rubber disk 50 which is held in place by a rivet 52 that is integral with mask 18.

Another one-way valve is positioned at the end of coupling 38 which is received within inlet opening 26 of mask 18. This valve is designated generally by the numeral 54 (see FIG. 4) and again comprises a light weight flexible rubber disk 56 which is seated upon a supporting framework 58. Gussets 58a of the framework mount a rivet 60 which holds disk 56 in place.

It is to be noted, of course, that each conduit 32 follows a generally curvilinear path over the head 12 and terminates at the back of the neck. A strap 62 is secured to each of the conduits 32 and serves to hold the conduits in place on the head. A head covering 64 is illustrated in broken lines in FIG. 1 and completely covers the major portion of both of conduits 32 as well as head 12. Covering 64 is secured to the head by strap 66. It is to be understood that head covering 64 may either be pulled on over the conduits or the latter together with their associated sack 30 may be joined with the head covering and the entire assembly placed over the head at once.

When the device of the present invention is to be utilized, it is placed over the head and face of a wearer with mask 18 covering the nose and mouth as previously described. It is, of course, important to secure the mask in a manner to present the best possible fit so as to preclude air from passing between the edges of the mask and the face of the wearer. Air will pass into conduit 32 through intake 34 and during inhalation valve 54 will move to the open position illustrated in broken lines in FIG. 4. During this time, valves 48 covering outlet openings 28 will remain closed. As the person exhales valve 54 will close and valves 48 will open in the manner illustrated in FIG. 3 so as to accommodate air flow in the direction of the arrows. The exhaled air will pass into sack 30 where it will be held for a period of time in heat exchange relationship with conduit 32 and the incoming air. The exhaled air is, of course, also in heat exchange with the heat of the body emanating from head 12. Since heat lost through the head accounts for approximately 50% of total body heat loss, the temperature of the exhaled air will be appreciably raised by virtue of the heat exchange relationship with the head. This provides additional heat for exchange with the incoming air in conduits 32. Exit opening 32c at the end of sack 30 near opening 34 allows for eventual escape of exhaled air in the sack. This opening is far enough removed from air intake 34 so as to avoid inhalation of carbon dioxide. During exhalation moisture will condense in mask 18 particularly in the vicinity of inlet opening 26. This moisture will help to humidify the incoming air further increasing the comfort of the person who is breathing the air.

It is important for proper operation of the device of the invention that the combined inside diameter of conduits 32 be at least equal to approximately 20 mm. This is approximately the diameter of the adult trachea thereby assuring adequate and unrestricted air flow to meet lung capacity.

By virtue of the fact that full advantage is taken of the nearly fifty percent (50%) loss of body heat through the head, as well as the added heat from the expired air, warming of the inhaled air is substantially enhanced over what is achieved with prior art devices. In an extremely cold environment, head covering 64 may include as part of its construction a light weight, flexible insulating type of material sold under the commercial trademark Space Blanket thus retarding heat transfer from the head and increasing the effective heat exchange between sack 30 and head 12. If head covering 64 is omitted it may be desirable to construct sack 30 so that each of the portions 32b has one side of relatively thin, non-reflective material for placement next to the head with the other side being formed of a material such as Space Blanket previously described.

While the invention has been particularly described in conjunction with use by a wearer in cold environments, it may also be utilized by workers who are exposed to high temperatures and wear protective clothing around their bodies. The exhaled air in this instance will cool the incoming air prior to inhalation.

I claim:

1. A breathing device comprising:
   a mask for convering the mouth and nose of a wearer, said mask having an inlet and an outlet;
   air intake conduit means having an outlet in communication with the inside of said mask,
   said conduit means adapted to be disposed in a curvilinear path along a substantial portion of the head of the wearer and having an inlet remote from said outlet for air passage;
   means for closing said air intake conduit means outlet during exhalation of air by said wearer; and
   sack means for enclosing said air intake conduit means over substantially the entire length thereof and therefore, along a substantial portion of the head of the wearer thereby being in heat exchange communication with the head of the wearer,
   said sack means being disposed in communication with said mask outlet and having an opening for egress of air remote from the place of communication with said outlet whereby, heat from exhaled air as well as body heat normally lost through radiation from the head adjusts the temperature of air to be inhaled.

2. The invention of claim 1, wherein is included second air intake conduit means having an outlet in communication with said mask, said second conduit means adapted to be disposed in a curvilinear path along a substantial portion of the head of the wearer and having an inlet remote from said outlet for air passage; means for closing said second conduit means outlet during exhalation of air by said wearer; second sack means for enclosing said second air intake conduit means over substantially the entire length thereof and therefore, along a substantial portion of the head of the wearer thereby being in heat exchange communication with the head of the wearer, said second sack means being disposed in communication with said mask outlet and having an opening for egress of air remote from the place of communication with said outlet whereby, heat from exhaled air as well as body heat normally lost through radiation from the head adjusts the temperature of air to be inhaled.

3. The invention of claim 2, wherein is included means for closing said means outlet during inhalation of air from said conduit means.

4. The invention of claim 3, wherein is included means for holding said conduit means on the head of a wearer of said device.

5. The invention of claim 4, wherein is included means for covering the head of said wearer along with the major portion of each of said conduit means.

6. The invention of claim 4, wherein is included means for holding said conduit means on the head of a wearer of said device.

7. The invention of claim 4, wherein is included means for releasably securing each of said first and second sack means to said mask.

8. A method of regulating the temperature of air being breathed by a person, said method comprising:
   capturing air exhaled by said person;
   directing said exhaled air over the head of said person for heat exchange therewith;
   passing air to be inhaled through said exhaled air for heat exchange therewith and with the head area.

9. A method as set forth in claim 8, wherein is included the step of exhausting said exhaled air after a period of heat exchange relationship with said air to be inhaled.

10. A method as set forth in claim 9, wherein is included the step of covering the head of said person to help retain body heat for heat exchange with said exhaled and inhaled air.

* * * * *